US008906324B2

(12) United States Patent
Jalenques

(10) Patent No.: US 8,906,324 B2
(45) Date of Patent: Dec. 9, 2014

(54) AUTOMATIC INOCULATING SYSTEM AND METHOD FOR DEPOSITING A SAMPLE ON A SUBSTRATE IN A PATTERN

(71) Applicant: INTERLAB, St Nom la Breteche (FR)

(72) Inventor: Emmanuel Jalenques, St Nom la Breteche (FR)

(*) Notice: Subject to any disclaimer, the term of this patent is extended or adjusted under 35 U.S.C. 154(b) by 0 days.

(21) Appl. No.: 13/903,104

(22) Filed: May 28, 2013

(65) Prior Publication Data

US 2013/0260038 A1    Oct. 3, 2013

Related U.S. Application Data

(63) Continuation-in-part of application No. 12/791,044, filed on Jun. 1, 2010, now abandoned.

(30) Foreign Application Priority Data

Jun. 2, 2009  (FR) ...................................... 09 02644

(51) Int. Cl.
 *B01L 3/02* (2006.01)
 *C12Q 1/24* (2006.01)
 *B05C 5/02* (2006.01)
 *C12M 1/26* (2006.01)

(52) U.S. Cl.
 CPC . *B05C 5/02* (2013.01); *C12M 33/04* (2013.01)
 USPC .......... 422/509; 422/501; 422/511; 422/544; 422/546; 422/63; 422/64

(58) Field of Classification Search
 CPC . G01N 35/025; G01N 35/10; G01N 35/1009; G01N 35/1011; B05C 5/02; C12M 33/04; C12M 33/06
 USPC ............. 422/501, 509, 511, 544, 546, 63–64
 See application file for complete search history.

(56) References Cited

U.S. PATENT DOCUMENTS 5,479,969 A * 1/1996 Hardie et al. ................. 141/130
5,955,373 A * 9/1999 Hutchins et al. ............... 436/48

* cited by examiner

*Primary Examiner* — Brian R Gordon
(74) *Attorney, Agent, or Firm* — O'Connell Law Firm; Thomas P. O'Connell

(57) ABSTRACT

An automatic inoculating system for depositing a sample on a substrate in a predetermined pattern. A turret is rotatable about a vertical axis, and an arm retained by the turret is pivotable about a horizontal axis. A stylus retained at a distal portion of the arm sucks up and dispenses the sample, such as by use of a pumping system in fluidic communication with the stylus. A support rotatably retains the substrate. The arm can be raised and lowered, such as by a cylinder on which the arm rests without a retaining mechanical connection therebetween. The arm can thus freely lift off the cylinder as when the stylus contacts the surface of the substrate. The sample can thus be deposited on the substrate in a predetermined pattern by a dispensing from the stylus in combination with rotation of the turret and the substrate and a pivoting of the arm.

17 Claims, 4 Drawing Sheets

AUTOMATIC INOCULATING SYSTEM AND METHOD FOR DEPOSITING A SAMPLE ON A SUBSTRATE IN A PATTERN

FIELD OF THE INVENTION

The present invention relates to the field of automatic devices for inoculating a culture substrate with a sample to be analyzed, usually a substantially liquid sample. It relates more particularly to a system to take and inoculate the sample, for example, on a substrate in a Petri dish.

BACKGROUND OF THE INVENTION

In an automatic inoculating device, each sample is taken in a sample tank by the automatic device using a stylus. The sample is then distributed on the substrate surface using the same stylus. Between each inoculation, it is proper to clean the stylus to avoid contamination of the next sample.

In automatic devices of the prior art, the stylus is dipped in several tanks. The first tank may contain a disinfectant, and the following tanks may contain sterile water for rinsing the disinfectant. Such a system and method is described in, for example, U.S. Pat. No. 5,547,872 o Schalkowsky et al.

The stylus is typically moved from one area of sample collection in the corresponding tank to an inoculating area in which the sample is distributed, generally in a spiral pattern, then to each cleaning station and then into each cleaning tank. The stylus typically moves linearly through, for example, a drive rack.

At each position, the stylus must be lowered or raised, for example, to dip into the sample tank or in a tank of cleaning fluid.

The maintenance of the devices of the prior art is delicate. In addition, typical prior art devices do not have satisfactory reliability necessary to producing consistent patterns of inoculation.

The present invention thus seeks to provide a system that can overcome the previously mentioned drawbacks of the prior art. In particular, the inoculating device taught herein is constructed to be relatively simple and inexpensive in construction, operation, and maintenance thereby allowing for easy, reliable, and efficient handling of samples and, potentially, cleaning products.

SUMMARY OF THE INVENTION

According to the invention disclosed herein, an automatic inoculating device for a sample on a substrate has a mobile turret that is rotatable about an axis of rotation, preferably about a substantially vertical axis of rotation. An arm mobile is rotatable about an axis in relation to the turret, preferably about a substantially horizontal axis. The arm may be carried by the turret. A distal end of the arm includes means for retaining a stylus at a distal portion of the arm, and means are provided for raising and lowering the arm.

The means for raising and lowering the arm can, for example, take the form of a piston that is movable between bottom and top positions. The piston can be disposed near but spaced from the axis of the arm, and the arm can rest atop an upper end of the piston, possibly without being mechanically attached thereto. With that, the arm can freely lift off of the top of the piston, such as when the stylus makes contact with a surface, such as the surface of the substrate.

The means for retaining the stylus can preferably retain the stylus such that it can be removed from the distal portion of the arm without tools. That can, by way of example, be carried out by a ring fixed to the stylus in combination with a housing retained in the distal portion of the arm where the housing removably receives the ring. The ring can, for example, be fixed, preferably glued, to the stylus. Where the ring is fixed to the stylus, such as by gluing, it is more convenient to remove and replace a given kit of such components to achieve predetermined functionality.

Means can be provided for axial and transverse positioning of the ring relative to the distal portion of the arm, and the housing or other means can act to retain the ring at the distal portion of the arm. The axial and transverse positioning means may include a conical surface on the ring in combination with a conical surface of the housing. The conical surfaces can have substantially the same angle. With that, the conical surface of the housing will tend to receive and trap the conical surface of the ring.

The means for axial and transverse positioning of the ring relative to the distal portion of the arm can further include an annular peripheral rib on the ring together with a nut engaged with the distal portion of the arm, such as by a threaded engagement with a cap. The nut thus cooperates with the rib to keep the ring fixed in relation to the distal portion of the arm and to retain the stylus.

The stylus can in certain embodiments comprise an extremity of a flexible pipe. The flexible pipe can be retained by a snap-lock connection mechanism such that it can be fully accessible, mountable, and removable without tools. To ensure that only the pipe may be contaminated by the sample, the pipe has preferably a length long enough that the pipe provides an internal volume sufficient to store a sample volume sufficient for an inoculation. So that such an extended length can be properly disposed in the controller of the inoculating system, a roller may be incorporated, and the flexible pipe can have a wound or helical configuration, such as by winding around a portion of the pipe. With that, the pipe can provide an internal volume capable of storing a sample volume sufficient for an inoculation.

Embodiments of the system can further include motorized pump, which can be disposed upstream of the pipe and in fluidic communication therewith. With that, the distal end of the flexible pipe forming the stylus can be employed to suck up and discharge a sample through the stylus.

At least one reserve with an interior for retaining a liquid product can be included. The pump can suck up the liquid product from the reserve through the stylus and then discharge the product from the stylus. In certain practices of the invention, there can be at least first and second reserves. Under such manifestations of the invention, the pump can use the stylus to draw two products, independently of one another, from the first and second reserves respectively. The products can be discharged independently by the stylus. By way of example, a disinfectant, such as an alcohol, can be disposed in the first reserve, and a rinse aid, such as distilled water, can be disposed in the second reserve.

Support for the substrate can, for example, take the form of a means for retaining a Petri dish. The Petri dish can contain the substrate, and the substrate can receive the sample.

The system thus disclosed can be employed to practice a process for inoculating a Petri dish. The process can begin by providing a system as taught herein. A sample can be provided as can be a substrate. A portion of the sample can be drawn into the stylus, and at least a portion of the sample can be deposited from the stylus onto the substrate in a pattern. The pattern can be based on a coordinated, such as simultaneous, rotation of the substrate and a rotation of the turret. As taught herein, the sample can be automatically deposited on the substrate in a predetermined pattern. The axis of rotation of the turret can be substantially vertical, and the axis of rotation of the arm can be substantially horizontal.

In a particular practice of the invention, the system can comprise an automatic inoculating device for a sample on a substrate. The system can be considered to be founded on a turret rotatable about an axis of rotation. An arm is carried by the turret, and the arm is rotatable about an axis in relation to the turret. A stylus is provided for sucking up and dispensing the sample, and means are provided for retaining the stylus at a distal portion of the arm. A substrate can be retained, such as within a Petri dish, by a support, which can include a means for rotating the substrate. Means can be provided for raising and lowering the arm in the form of a cylinder extendable and retractable between bottom and top positions. The cylinder can be disposed spaced from the axis of the arm, and the arm can rest on an upper end of the cylinder, possibly with no restraining mechanical connection therebetween. With this, a movement of the cylinder will produce a raising or lowering of the arm, and the arm can lift off of the upper end of the cylinder when necessary or desirable, such as when the tip of the stylus makes sufficient contact with a surface. Under such a system, the sample can be deposited on the substrate in a pattern by a dispensing from the stylus in combination with a rotation of the turret and a movement of the arm, possibly in combination with a rotation of the substrate. Moreover, with the tip of the stylus performing the sucking up and dispensing, the entire container of the sample need not be moved for such operations. Instead, the sample can be remotely accessed through the flexible pipe.

BRIEF DESCRIPTIONS OF THE DRAWINGS

Several embodiments of the invention are described below, as examples of possible manifestations of the system and method disclosed herein, with reference to the accompanying drawings in which.

DETAILED DESCRIPTION OF PREFERRED EMBODIMENTS

The system and method disclosed herein are subject to a wide variety of embodiments. However, to ensure that one skilled in the art will be able to understand and, in appropriate cases, practice the present invention, certain preferred embodiments of the broader invention revealed herein are described below and shown in the accompanying drawing figures. Therefore, before any particular embodiment of the invention is explained in detail, it must be made clear that the following details of construction and illustrations of inventive concepts are mere examples of the many possible manifestations of the invention.

Figure 1:
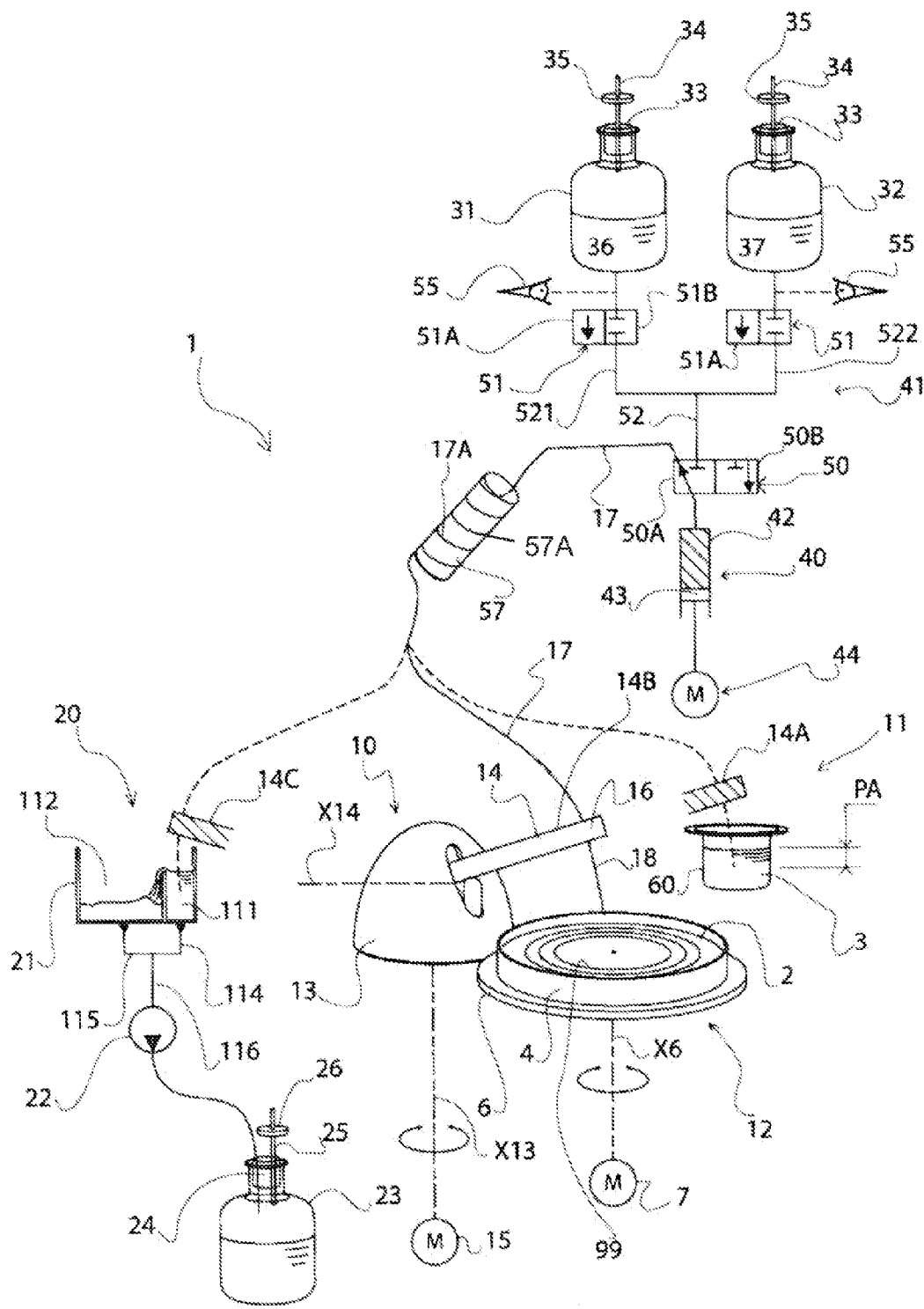
FIG. 1 is a schematic depiction of an automatic inoculating device according to the invention in operation.

FIG. 1 illustrates an automatic system 1 according to the invention for inoculating a substrate 2 with a sample 3 to be analyzed. In the illustrated example, the substrate 2 is contained in a Petri dish 4 in the form of a gel, and the sample 3 is substantially liquid.

The illustrated system 1 includes a supply area 11 for the sample 3 to be tested and an inoculating area 12. The system 1 includes a collecting mechanism 10 for collecting the sample 3 in the supply area 11 and depositing it, at least partially, on the surface of the substrate 2. The automatic system 1 includes a tray 6 that is rotatable about a vertical axis X6. The tray 6 constitutes a support for the Petri dish 4. The tray 6 and any retained Petri dish 4 can be at least indirectly rotated around axis X6 by a motor 7.

Figure 4:
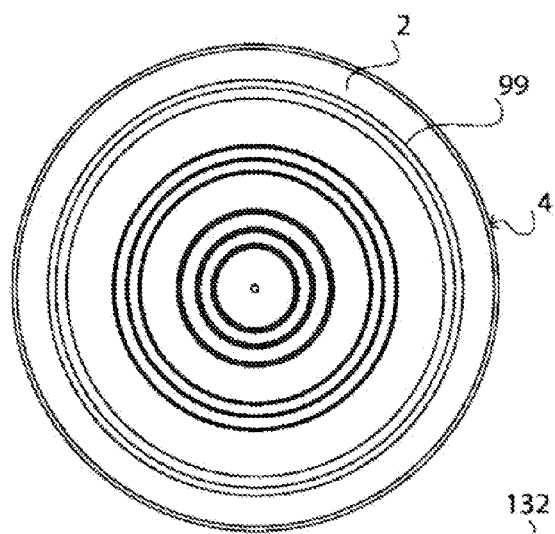
FIGS. 4 and 5 are top plan views of inoculation patterns as dispensed according to the invention.
Figure 5:
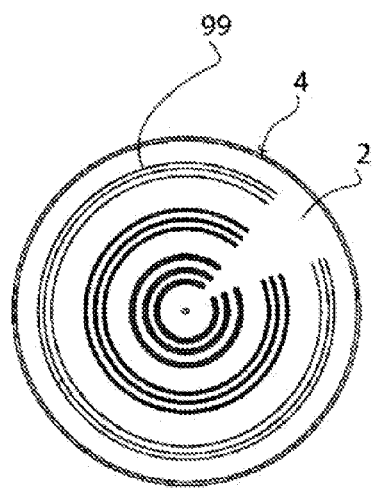

A method of inoculating according to the invention is more particularly described with additional reference to FIGS. 4 and 5.

Figure 2:
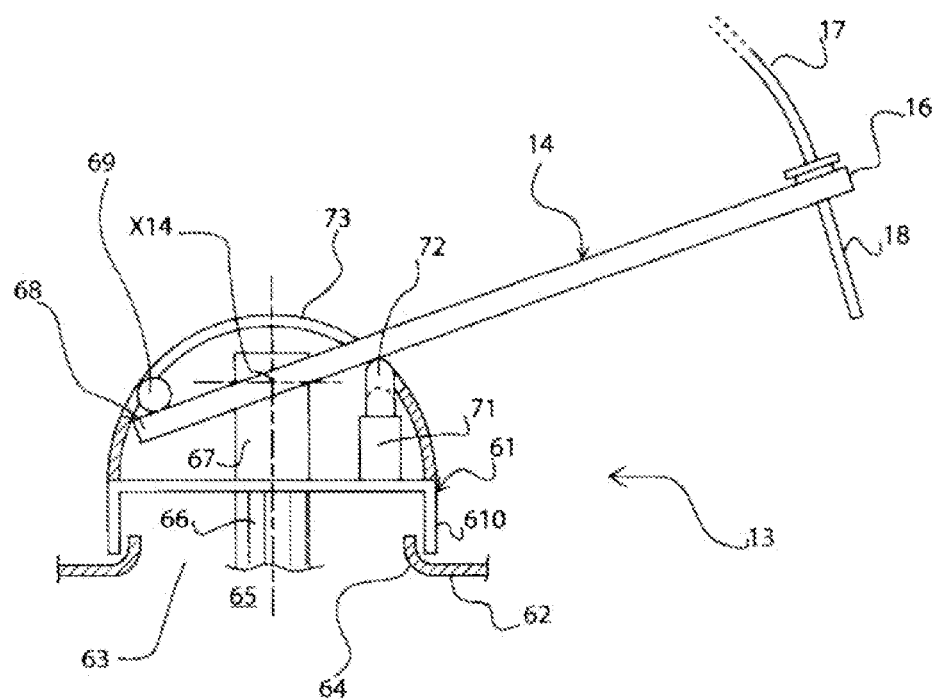
FIG. 2 is a partially sectioned elevational view schematically depicting a system according to the invention for the supply of the automatic device of FIG. 1, the system having an arm mounted on a rotating turret.
Figure 3:
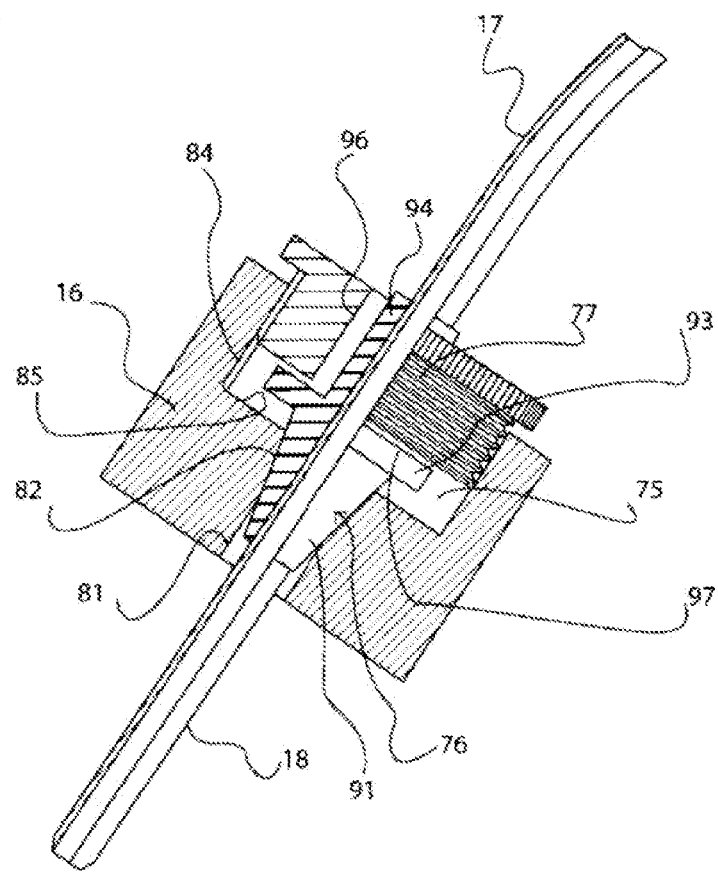
FIG. 3 is a partially-sectioned view of means for retaining a stylus relative to the to a distal portion of the arm of FIG. 2.

A turret 13, which will be described in more detail with reference to FIGS. 2 and 3, is rotatable about a vertical axis X13, such as by operation of a motor 15. An arm 14 is retained by the turret 13. The arm 14 is movable in a vertical plane in relation to the turret 13, such as by a pivoting about a substantially horizontal axis X14 in relation to the turret 13. A distal portion 16 of the arm 14 retains a flexible tube or pipe 17. A distal end or extremity 18 of the pipe 17 extends downwardly from the arm 14 to form a stylus 18.

Preferably, the flexible tube or pipe 17 is made of a material, such as example POLY (TETRAFLUOROETHYLENE), that resists adhering in relation to the sample 3. This arrangement is particularly advantageous in that it limits adhesion, especially when a sample 3 has a relatively thick and sticky consistency.

The automatic system 1 of FIG. 1 further includes cleaning system 20 for the stylus 18. In the illustrated example, the cleaning system 20 includes a pour tank 21, a draining mechanism 22 for discharging effluent from the cleaning tank 21 to a retention vessel 23 for the aforesaid discharged effluents by pumping. In the example shown, the draining mechanism 22 includes a diaphragm pump 22. The retention vessel 23 is closed by a plug 24. The plug 24 is pierced by a vent 25, having the shape of a pipe. This pipe vent 25 is equipped with a filter 26 of 0.2 μm, so the atmosphere is protected from any possible microbial contamination. The pour tank 21 and its use will be more particularly described with reference to FIG. 7.

The automatic system 1 of FIG. 1 also includes reserves 31 and 32 for containing liquid for cleaning the stylus 18. Preferably, each of these reserves 31 and 32 is removable and can be replaced by a full one when necessary. Each reserve 31, 32 is shaped like a bottle and can be closed by a plug 33 with a vent 34 for maintaining the interior thereof at atmospheric pressure as to the transfer of liquid it contains. Each vent 34 is fitted with a filter 35, such as a filter 0.2 μm, to ensure the sterility of the liquid contained in the corresponding reserve 31, 32. An initial reserve 31 of the two reserves contains a disinfectant 36, alcohol 36 in the example shown. The second reserve 32 contains a rinse aid 37, distilled water 37 in the example shown.

The automatic system 1 further includes a pumping system 40 upstream of and in fluidic communication with the flexible pipe 17 and thus the stylus 18. A supply 41 is provided for fluids 3, 36, 37 manipulated by the automatic system 1. In the example illustrated, the pumping system 40 comprises a syringe 40 with a cylinder 42 in which slides a piston 43. The piston 43 can be driven by a motor 44, preferably a stepper motor 44.

Supplying means in this embodiment takes the form of three valves, namely a first valve 50 and second and third valves, each indicated at 51. The first valve 50 has two positions. In the first position, shown in FIG. 1, the valve 50 can suck up or reject a fluid through the pipe 17. The second position of the first valve 50 allows connecting the syringe 40 with a supplying pipe 52 for cleaning fluid 36, 37. The pipe 52 comprises two parts 521 and 522, each engaging with a respective reserve 31, 32 of cleaning fluid.

Each of the second and third valves 51 is assigned to a respective reserve of 31, 32 that retains cleaning fluid 36, 37. In a first, opened position 51A, each valve 51 allows fluid to flow in the respective pipe 52. In a second, closed position 51B, shown in FIG. 1, each valve 51 prevents the respective liquid to flow out through pipe 52.

A sensor 55 is arranged on each side branch 521, 522. The sensor 55 is provided to detect the absence or presence of liquid in the side branch 521, 522. The absence of liquid in one of the side branches 521, 522 can induce a stopping of the automatic system 1 pending the replacement or filling the corresponding reserve 31, 32.

The sample 3 is preferably taken from the pipe 17 sufficiently downstream from the syringe 40 so that the syringe 40 cannot be contaminated by the sample 3. More particularly, the pipe 17 in this embodiment is provided with a sufficient length so that its internal volume can contain a sufficient sample for inoculating. To enable the arrangement of this length of the pipe 17 inside of the automatic system 1, the system 1 includes a retaining member comprising a cylindrical roller 57 around which is wound in a helical coil a coiled portion 17A of the pipe 17. Preferably, the roller 57 includes a shaped screw thread or groove along which the pipe portion 17A can be arranged. Also preferably, the pipe portion 17A can be engaged with the screw thread or groove by an interlocking, snap-fit connection mechanism as shown, for example, in FIG. 1. The snap-fit engagement could be achieved in a number of ways according to the invention, including, by way of example, a frictional, snap-fit reception of the coiled portion 17A within a correspondingly sized channel 57A in the roller 57. With that, the pipe portion 17A can be removed from the roller 57 by hand without the need for tools, such as by pulling the coiled portion 17A out of the channel 57A or out of whatever other snap-fit engagement might be employed. Thus arranged, the pipe 17 is visible and accessible throughout its length.

Figure 6:
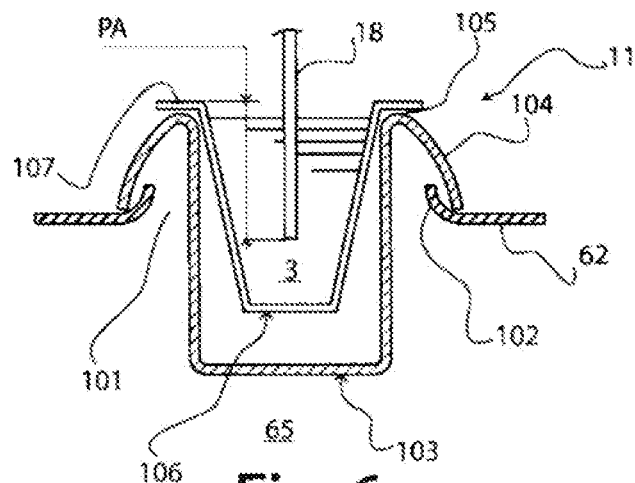
FIG. 6 is a sectioned elevational view of a storage and sampling area for a product to be inoculated in the automatic device of FIG. 1.
Figure 7:
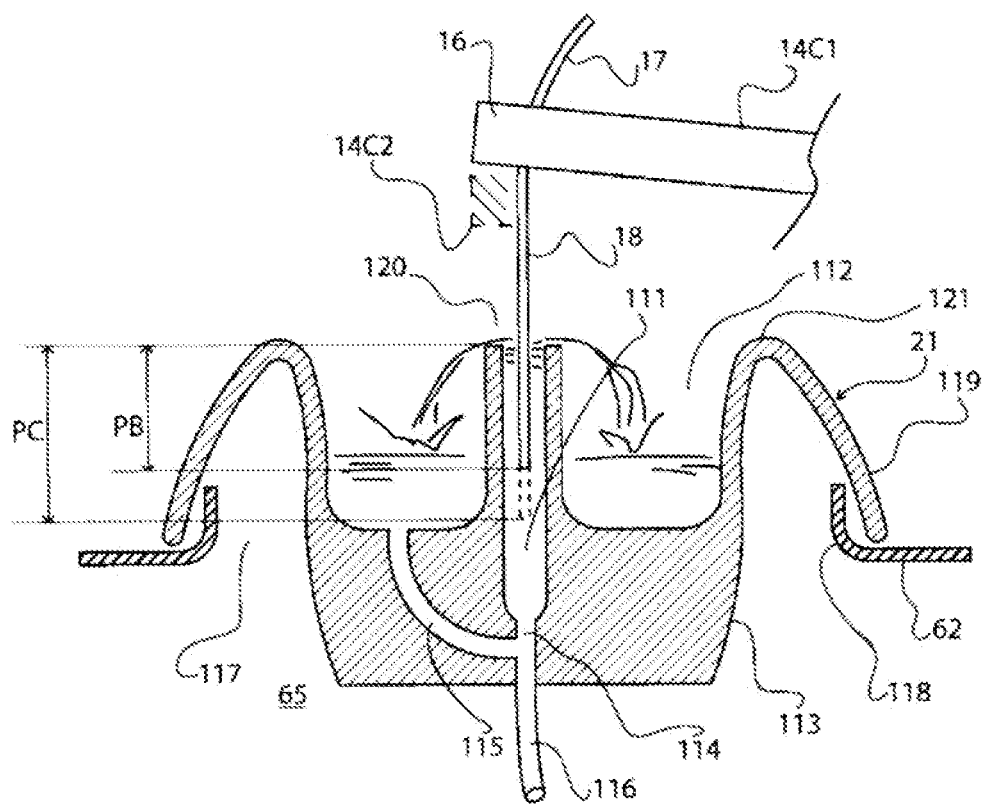
FIG. 7 is a sectioned elevational view of means for cleaning the stylus of FIG. 3.

In the present example, as suggested in FIGS. 2, 6, and 7, the automatic system 1 includes a stainless steel body 62 on which are arranged the various elements that comprise the system 1. The body 62 includes a substantially horizontal platform, which is also indicated at 62 in FIGS. 2, 6, and 7.

A cycle of inoculating by use of the system 1 can begin with a sample 3 being stored in a supply area, for example in a container 60 as in FIG. 1. The arm 14 can then be brought in a sampling position 14A so that the stylus 18 is above the container 60. The arm 14 is then lowered so that the stylus 18 dips to a depth PA into the sample 3. With the valve 50 in position 50A, a sufficient portion of the sample 3 can be sucked into the pipe 17 using the syringe 40. The arm 14 is then raised and brought into a position 14B by rotating the turret 13 around its axis X13, as illustrated in FIG. 1, for the inoculation of the substrate 2. The arm 14 is lowered again so that the stylus 18 is close enough to the substrate 2 to deposit the sample 3 with the desired precision. By a combination of rotations of the turret 13 around its axis X13 and the platform 6 around its axis X6, the sample 3 can be automatically deposited according to a previously defined pattern. The pattern can, by way of example and not limitation, be a spiral, a combination of points and, additionally or alternatively, circles, arcs of concentric circles, or any other of a wide variety of configurations as can be appreciated with reference to FIGS. 4 and 5.

Once inoculating is completed, the arm 14 is raised and taken to a cleaning position 14C by rotation of the turret 13 around its axis X13 thereby to permit a cleaning of the stylus 18. The remaining sample 3 still in the pipe 17 is expelled into the discharge tank 21, such as by use of the syringe 40 with the first valve 50 in the position 50A. Then, the arm 14 can be lowered to dip the stylus 18 in the discharge tank 21.

With the valve 50 placed in the position 50B, the third valve 51 kept closed in position 51B, and the second valve 51 placed in position 51A, the syringe 40 is operated so that it fills with alcohol 36. Then, the positions of the first valve 50 and the second valve 51 are reversed, and the piston 43 is pushed inside the cylinder 42 so that the alcohol 36 is expelled into the tank 21 traversing the entire length of the pipe 17. The inside of the pipe 17 is thus fully disinfected. The exterior of the pipe 17 at the location of the stylus 18 is disinfected since the tank 21 is filled with alcohol.

The valve 50 can be returned to the position 50B, the second valve 51 kept closed in position 51B, the third valve 51 placed in the position 51A, and the syringe 40 can be operated to fill with distilled water 37. Then, the positions of the first valve 50 and the third valve 51 are reversed, and the piston 43 is pushed inside the cylinder 42 so that distilled water is expelled into the tank 21 traversing the entire length of the pipe 17. The inside of the pipe 17 is thus thoroughly rinsed. The exterior of the pipe 17 at the location of the stylus 18 is flushed since the tank 21 is filled with distilled water 37.

With the foregoing completed, a new cycle can be started.

The sample 3 is maintained downstream of the syringe 40. The syringe 40 and the portion of the pipe 17 upstream of the syringe 40 contain alternatively only alcohol 36 or water 37. That residual water 37 serves as a liquid piston between the piston 43 of syringe 40 and the sample 3 when the sample 3 is handled, first to take it in and then to inoculate it.

The turret 13 can be further understood with reference to FIG. 2. A turret base 61 comprises a substantially disc-shaped portion and is equipped with a peripheral skirt 610. The platform 62 includes a circular orifice 63. A raised edge 64 is formed in the platform 62 in the periphery of the orifice 63. The skirt 610 is provided for covering the raised edge 64, so that they contribute together to prevent the penetration of liquid and, additionally or alternatively, of solid inside the body 65 of the automatic system 1.

A drive mechanism 66 extends below the base 61 to inside the body 65. The drive mechanism 66 is driven, at least indirectly, by the motor 15 of the turret 13 as in FIG. 1. The base 61 also carries an upstanding support shaft 67 that provides a horizontal axis X14 for the arm 14 and thus pivotally supports the arm 14. Opposite the distal portion 16 of the arm 14 relative to the axis X14, the arm 14 includes a proximal extremity 68 on which is fixed a counterweight 69. With that, the arm 14 is calibrated to have a fail over that permits an upward pivoting of the distal portion 16 of the arm 14 substantially without effort, and that upward pivoting is readily permitted since there is no retaining mechanical connection between the arm 14 and cylinder 71, which is described below. The proximal extremity 68 and the counterweight 69 in this example are directly above the base 61.

A cylinder 71 with a vertically extendable and retractable distal portion 72 extends vertically upward from the base 61.

The cylinder 71 in this embodiment is placed close to the support shaft 67 between the support shaft 67 and the distal portion 16 of the arm 14. The arm 14 rests by its own weight on the upper end of the distal portion 72. Under this construction, the arm 14 is movable in a vertical plane carried by the turret 13 as the distal portion 16 of the arm 14 is raised or lowered by selective extension or retraction of the distal portion 72 of the cylinder 71. A hemispherical cap 73 covers and protects the inside of the turret 13.

As disclosed herein, the arm 14 merely rests on the upper end of the cylinder 71 without a retaining mechanical connection between the arm 14 and the cylinder 71. As a result, the arm 14 rests on the upper end of the cylinder 71 only under the force of gravity, and the arm 14 can freely lift off of the upper end of the cylinder 71, such as when the tip of the stylus 18 makes contact with a surface, such as the surface of the substrate 2.

FIG. 3 depicts a particular construction for fastening the pipe 17 to the distal portion 16 of the arm 14. This assembly includes the elements described below, each potentially rotatable, and all mounted coaxially. A housing 75 is formed in and extending through the distal portion 16 of the arm 14 from an upper face to a lower face thereof. A ring 76 is coupled to the pipe 17, such as by gluing or any other method, with the part of the pipe 17 extending beyond the ring 76 forming the stylus 18. A threaded nut 77 maintains the ring 76 in relation to the housing 75 and the distal portion 16 of the arm 14 in general.

The housing 75 includes, from the lower face to the upper face of the arm 14, a cylindrical portion 81 of small diameter but sufficient for the stylus 18 to be inserted therethrough, then a widening conical portion 82, and then a cylindrical portion 84 of large diameter forming with the conical portion an interior portion or escarpment 85. The interior portion 85 is threaded for threadedly engaging the nut 77.

The ring 76 comprises, upstream to downstream, a conical portion 91 gradually widening at an angle identical to the conical portion 82 of the housing 75. The conical portions are provided to cooperate each other to position transversely and longitudinally the ring 76 in the housing 75 and the stylus 18 relatively to the extremity 16 of the arm 14. The conical portion 82 of the housing 75 thus receives and retains or traps the conical portion 91 of the ring 76. The largest diameter of the portion 91 is greater than the largest diameter of the portion 82, so that the portion 91 extends beyond the portion 82 inside the cylindrical portion 94. Beyond the conical portion 91, the ring 76 includes an annular rib 93 extending radially beyond the conical portion 91, and a cylindrical portion 94 extending longitudinally away from the rib 93.

The nut 77 includes an axial cylindrical drilling 96, provided for the passage of the cylindrical portion 94 of the ring 76, and an anterior face 97 that bears on the rib 93 of the ring 76. Thus, when assembled, the nut 77 threadedly engages the tapping of the housing 75, and the anterior surface of the nut 77 comes to bear against the rib 93 and keeps the ring 76 in position in the housing 75. Thus, the stylus 18 is maintained in a fixed and defined position relative to the distal portion 16 of the arm 14.

The described system 1 provides improved inoculating of a Petri dish 4. In automatic devices of the prior art, the sample is inoculated in a pattern forming a spiral on the substrate. The pattern is achieved by moving the stylus radially at a constant linear speed while the Petri dish turns at a constant angular velocity. This allows a gradually reduction of the surface density in the sample as the distance from the center of the Petri dish increases. However, the interpretation of the results of such processes is complicated and requires special charts specific to the individual inoculating device. The risks of misinterpretation are important.

It is proposed according to the present invention to produce patterns as, for example, concentric circles 99. The density varies with the distance from the center of the Petri dish 4, as in the spirals of the prior art. However, the density remains constant within a given circle. As a result, the interpretation of results is simplified because it no longer depends on the subtended angle under which the result of the culture is analyzed.

In the example shown in FIG. 4, the pattern includes three groups of three close circles 99 together. The circles 99 of each group are very close. As a result, they have very similar densities. Thus, each group corresponds noticeably to a determined concentration. To improve the accuracy of the results, the automatic system 1 disclosed herein advantageously comprises means for varying the speed of rotation of the Petri dish 4. With that, the density of circles 99 in the same group can be rendered substantially identical.

In the operating mode of FIG. 5, shown on a reduced scale, the pattern is confined to arcs of circle 99. This pattern produced similar results. However, it avoids depositing the sample on previously inoculated areas when achieving the circles 99.

The sampling area 11 can be better understood with reference to the depiction of FIG. 6. The area 11 includes a circular orifice 101 in the platform 62. The peripheral edge of the orifice 101 has a raised edge 102. A cylindrical tank 103 is disposed in the orifice 101. A skirt 104 extends from the upper edge 105 of the container and comes to rest on the platform 62 around the aforesaid raised edge 102. The skirt 104 covers the aforesaid raised edge 102 so that they cooperate to prevent the penetration of liquid and, additionally or alternatively, solids into the body 65 of the automatic system 1.

The product to be inoculated, namely the sample 3, is contained in a cup 106 whose upper edge 107 rests on the upper edge 105 of the container 103. Thus, a sample 3 may be supplied or removed from the automatic system 1 without risk of spilling in the body 65 of the system 1 that remains protected by the container 103. In addition, portions of the sample 3 spilled in the container 103 can be cleaned since the container 103 is removable for cleaning. As is also shown in FIG. 6, the stylus 18 is expected to dip of a depth PA, measured at the edge 107 of the cup 106, during the taking of the sample 3.

We will now describe the operation of the discharge or pour tank 21 and the cleaning process with reference to FIG. 7. The pour tank 21 has substantially a shape of revolution around a vertical axis. The pour tank 21 includes two coaxial bowls 111, 112, which have a common base 113. The interior bowl 111 is designed specifically to receive the stylus 18 and cleaning fluids 36, 37. The shape of the interior bowl 111 is narrow. As a result, it offers radially sufficient, but not excessive, space for receiving the stylus 18 and allowing a flow of liquid 36, 37 around the stylus 18. The outer bowl 112 is designed to recover liquid overflowing from the interior bowl 111. The bowls 111, 112 have drain pipes 114, 115 respectively formed in the base 113. The drain pipes 114, 115 join to form a unitary drain pipe 116, which is connected to the emptying pump 22 shown in FIG. 1.

Like the turret 13 and the container 103, the discharge tank 21 is inserted into an orifice 117 of the platform 62. The tank 21 includes a skirt 119 that extends from an upper edge 121 of the outer bowl 112 and covers a raised edge 118 of the orifice 117. The interior 65 is thus protected, and the tank 21 is easily removable, such as for cleaning.

Looking again to FIG. 1, when inoculating the substrate 2 is completed as previously described, the extremity of the arm 14 is rotated to a position 14C in which the stylus 18 is disposed above the tank 21, preferably above the outer bowl 112. With that, the pipe 17 can be purged of portions of the sample 3 not used for inoculating.

With reference to FIG. 7, the arm can then be moved to position 14C1 in which the stylus 18 is dipped at a depth of PB into the interior bowl 111. The stylus 18 is maintained at this position during the disinfecting operation. As previously described, during this operation, alcohol 36 flows through the pipe 18 so it drains out of the stylus 18. Alcohol 36 then fills the interior bowl 111 above its upper rim 120 causing it to overflow to the outer bowl 112. Thus, the level of alcohol in the interior bowl 111 tends to remain consistent, substantially equal to the upper rim 120 of the bowl 111. The depth PB is chosen to be higher than the PA taking depth of the sample in the bowl 106. This step ensures the external disinfection of the stylus 18 to any height that may have been contaminated during the taking of the sample 3.

The arm can then be moved to position 14C2 where the stylus 18 is dipped to a depth PC into the interior bowl 111. The stylus 18 is maintained in this position during the flushing operation. As previously described, during this operation, water 37 flows through the pipe 17 to drain out off the stylus 18. The water 37 then fills the interior bowl 111 and overflows to the outer bowl 112 over the upper rim 120. Thus, the water level inside the bowl 111 tends to remain consistent and substantially equal to the height of the upper rim 120 of the bowl 111. The depth PC is chosen higher than depth PB previously used for disinfection. This process ensures that alcohol 37 previously used for cleaning out the stylus 18 is thoroughly rinsed and will not unintentionally sterilize future inoculating.

Figure 8:
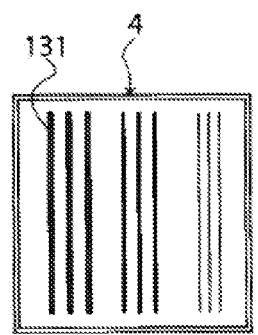
FIG. 8 is a is a top plan view of an inoculation pattern where the Petri dish is square and the inoculation pattern is made in the form of straight lines parallel to each other.
Figure 9:
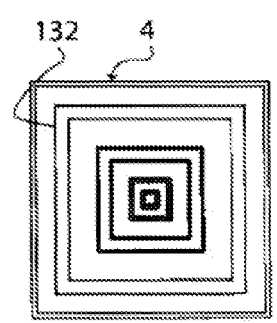
FIG. 9 is a top plan view of an inoculation pattern in the form of substantially homothetic squares.

FIGS. 8 and 9 illustrate two further modes of implementation for an inoculating method according to the invention. In these examples, the Petri dishes 4 are square.

In the example shown in FIG. 8, the inoculation is done in a form of straight lines 131 parallel to each other and having substantially the same length. Lines 131 are grouped into three groups of three lines 131. The lines 131 of the same group can have approximately equal densities, and lines 131 in separate groups can vary in density. For instance, the group of lines 131 depicted on the left in FIG. 8 has three lines of high density, the group of lines 131 on the right has three lines of low density, and the middle group includes three lines 131 of intermediate density.

In the example shown in FIG. 9, the inoculation is done in the form of straight lines grouped in squares 132. The squares 132 are homothetic themselves around the same center. The squares 132 are grouped into three groups of two squares 132. The lines of all the squares 132 of the same group can be of substantially consistent density. Here, for example, the interior group of squares 132 can include lines with high density, the outer group of squares 132 includes lines with low density, and the intermediate group of squares 132 includes intermediate-density lines.

Of course, the invention is not limited to the previous described examples. By way of example, except as the invention might be expressly limited, means for linear displacement of the stylus 18 may be provided rather than the rotating turret 13. Also, rather than being removable, the pour tank 21, the container 103, and other components can be fixed in place, such as by being stamped directly into the platform 62 of the automatic system 1. Still further, the pour tank 21, as schematically illustrated in FIG. 1, could vary in shape, such as by having a rectangular shape. The pour tank 21 can comprise two compartments 111, 112 separated by a wall for the pouring from one compartment 111, 112 to another 112, 111. As illustrated, other patterns can be provided rather than circles 99, and densities within patterns and within portions of patterns can be varied.

With certain details of the present invention for an inoculating system and method disclosed, it will be appreciated by one skilled in the art that changes and additions could be made thereto without deviating from the spirit or scope of the invention. This is particularly true when one bears in mind that the presently preferred embodiments merely exemplify the broader invention revealed herein. Accordingly, it will be clear that those with certain major features of the invention in mind could craft embodiments that incorporate those major features while not incorporating all of the features included in the preferred embodiments.

Therefore, the following claims are intended to define the scope of protection to be afforded to the inventor. Those claims shall be deemed to include equivalent constructions insofar as they do not depart from the spirit and scope of the invention. It must be further noted that a plurality of the following claims may express certain elements as means for performing a specific function, at times without the recital of structure or material. As the law demands, these claims shall be construed to cover not only the corresponding structure and material expressly described in this specification but also all equivalents thereof that might be now known or hereafter discovered.

The invention claimed is:

1. An automatic inoculating system for depositing a sample on a substrate in a pattern, the system comprising:
    a turret rotatable about an axis of rotation;
    an arm retained by the turret wherein the arm is pivotable about a pivot axis in relation to the turret,
    a stylus for sucking up and dispensing the sample wherein the stylus is retained at a distal portion of the arm;
    a pumping system fluidically connected to and upstream of the stylus to suck up and dispense the sample through the stylus;
    a rotatable support for the substrate; and
    a cylinder extendable and retractable between bottom and top positions wherein the cylinder is disposed spaced from the pivot axis of the arm and wherein the arm rests on an upper end of the cylinder whereby an extension or retraction of the cylinder produces a raising or lowering of the arm;
    whereby the sample can be deposited on the substrate in a pattern by a dispensing of the sample from the stylus in combination with a rotation of the substrate by the rotatable support, a rotation of the turret, and a pivoting of the arm.

2. The system of claim 1 wherein the arm rests on the upper end of the cylinder without a retaining mechanical connection between the arm and the cylinder whereby the arm rests on the upper end of the cylinder only under the force of gravity and whereby the arm can freely lift off of the upper end of the cylinder.

3. The system of claim 1 further comprising at least one reserve tank with an interior for retaining a liquid product so that the pumping system can suck up the liquid product from the reserve tank and then discharge the product through the stylus.

4. The system of claim 1 wherein the rotatable support for the substrate comprises a rotatable tray for supporting a Petri dish for containing the substrate.

5. The system of claim 1 wherein the axis of rotation of the turret is substantially vertical and wherein the pivot axis of the arm is substantially horizontal.

6. A process for inoculating a Petri dish using the system according to claim 1, the process comprising:
providing the system of claim 1;
providing a sample;
providing a substrate;
drawing a portion of the sample into the stylus; and
automatically depositing at least a portion of the sample from the stylus onto the substrate in a predetermined pattern based on a rotation of the substrate and a rotation of the turret.

7. An automatic inoculating system for depositing a sample on a substrate in a pattern, the system comprising:
a turret rotatable about an axis of rotation;
an arm retained by the turret wherein the arm is pivotable about a pivot axis in relation to the turret,
a stylus for sucking up and dispensing the sample wherein the stylus is retained at a distal portion of the arm;
a pumping system fluidically connected to and upstream of the stylus to suck up and dispense the sample through the stylus;
a rotatable support for the substrate; and
a raising and lowering mechanism for the arm wherein the raising and lowering mechanism is adjustable between bottom and top positions whereby an adjustment of the raising and lowering mechanism between the bottom and top positions produces a raising or lowering of the arm;
wherein the stylus is retained at the distal portion of the arm by a ring fixed to the stylus in combination with a housing retained in the distal portion of the arm wherein the housing removably receives the ring whereby the stylus can be removed from the distal portion of the arm;
whereby the sample can be deposited on the substrate in a pattern by a dispensing of the sample from the stylus in combination with a rotation of the substrate by the rotatable support, a rotation of the turret, and a pivoting of the arm.

8. The system of claim 7 wherein the stylus is retained at the distal portion of the arm further by a ring wherein the ring is axially and transversely positionable relative to the distal portion of the arm.

9. The system of claim 8 further comprising a housing in the distal portion of the arm wherein the ring is axially and transversely positionable by a conical surface on the ring and a conical surface of the housing wherein the conical surfaces have substantially the same angle whereby the conical surface of the housing can receive and retain the conical surface of the ring.

10. The system of claim 8 further comprising a peripheral rib on the ring and a nut threadedly engaged with the distal portion of the arm and wherein the ring is axially and transversely positionable by the ring, the peripheral rib, and the nut screwed onto the distal portion of the arm to cooperate with the rib to retain the stylus in relation to the distal portion of the arm.

11. An automatic inoculating system for depositing a sample on a substrate in a pattern, the system comprising:
a turret rotatable about an axis of rotation;
an arm retained by the turret wherein the arm is pivotable about a pivot axis in relation to the turret,
a flexible pipe wherein a distal end of the flexible pipe forms a stylus for sucking up and dispensing the sample wherein the stylus is retained at a distal portion of the arm;
a retaining member wherein the flexible pipe is retained relative to the retaining member by a snap-fit connection mechanism between the flexible pipe and the retaining member whereby the pipe is accessible and removable;
a pumping system fluidically connected to and upstream of the stylus to suck up and dispense the sample through the stylus;
a rotatable support for the substrate; and
a raising and lowering mechanism for the arm wherein the raising and lowering mechanism is adjustable between bottom and top positions whereby an adjustment of the raising and lowering mechanism between the bottom and top positions produces a raising or lowering of the arm;
whereby the sample can be deposited on the substrate in a pattern by a dispensing of the sample from the stylus in combination with a rotation of the substrate by the rotatable support, a rotation of the turret, and a pivoting of the arm.

12. The system of claim 11 further comprising means for retaining a portion of the flexible pipe in a coil whereby the pipe provides an internal volume within the coil to store a sample volume for inoculation.

13. The system of claim 12 wherein the means for retaining a portion of the flexible pipe in a coil comprises a retaining member wherein the portion of the pipe is wound around the retaining member.

14. The system of claim 13 wherein the retaining member comprises a cylindrical member.

15. The system of claim 14 wherein the flexible pipe is wound around the cylindrical member in a helical coil.

16. The system of claim 3 wherein there are at least first and second reserve tanks so that the pumping system can selectively draw two liquid products, independently of one another, from the first and second reserve tanks and discharge the products independently through the stylus.

17. The system of claim 16 further comprising a liquid disinfectant in the first reserve tank and a rinse aid comprising water in the second reserve tank.

* * * * *